US005690808A

United States Patent [19]
Akmal et al.

[11] Patent Number: 5,690,808
[45] Date of Patent: Nov. 25, 1997

[54] ELECTROCHEMICAL GAS SENSORS AND METHODS FOR SENSING ELECTROCHEMICAL ACTIVE GASES IN GAS MIXTURES

[75] Inventors: Naim Akmal, Hacienda Heights; Yining Zhang, Rowland Heights, both of Calif.

[73] Assignee: Teledyne Industries, Inc., Los Angeles, Calif.

[21] Appl. No.: 591,886

[22] Filed: Jan. 25, 1996

[51] Int. Cl.[6] .................................................. G01N 27/26
[52] U.S. Cl. .................. 205/775; 205/779.5; 205/785.5; 205/786.5; 204/412; 204/414; 204/421; 204/431; 204/432
[58] Field of Search .................................. 204/412, 414, 204/421, 431, 432; 205/779.5, 785.5, 786.5, 775

[56] References Cited

U.S. PATENT DOCUMENTS

| | | | |
|---|---|---|---|
| 2,805,191 | 9/1957 | Hersch | 205/785.5 |
| 2,992,170 | 4/1961 | Robinson | 205/785.5 |
| 3,124,520 | 3/1964 | Juda | 205/554 |
| 3,313,720 | 4/1967 | Robinson | 204/406 |
| 3,328,277 | 6/1967 | Solomans et al. | 204/412 |
| 3,454,485 | 7/1969 | Hauk et al. | 204/402 |
| 3,767,552 | 10/1973 | Lauer | 204/195 P |
| 4,077,861 | 3/1978 | Lauer | 204/195 P |
| 4,959,138 | 9/1990 | Brinkmann et al. | 204/414 |
| 4,960,497 | 10/1990 | Gallagher | 205/785.5 |
| 5,085,760 | 2/1992 | Razaq et al. | 205/785.5 |

FOREIGN PATENT DOCUMENTS

| | | |
|---|---|---|
| 06222038 | 8/1994 | Japan. |
| 6222038 | 8/1994 | Japan. |
| 969607 | 9/1964 | United Kingdom. |
| 969608 | 9/1964 | United Kingdom. |

OTHER PUBLICATIONS

"Gel–Silica Science" by L.L. Hench & W. Vasconceles in the Annual Review Material Science, 1990, vol. 20, pp. 269–298.

Full English language translation of JP06222038 (Fujiwara et al.), Aug. 1994.

JAPIO abstract of JP06222038 (Kunihiko et al.), Aug. 1994.

Primary Examiner—Kathryn L. Gorgos
Assistant Examiner—Alex Noguerola
Attorney, Agent, or Firm—Edward J. DaRin

[57] ABSTRACT

An electrochemical, galvanic type, oxygen sensor including scavenging electrodes for continuously reacting any unreacted or partially reacted active gases, such as oxygen, to remove the active gases prior to being dissolved or have been dissolved in the electrolyte resulting in less than accurate output signals. The use of the scavenging electrodes permits the gas sensor to detect active gases in a gas mixture in sub-parts per billion level accurately and without the need for external sparging of the electrolyte with a pure inert gas. The liquid electrolyte may be stored in the a sol-gel medium formed in sensor container and holding the electrolyte in voids or pockets in the medium thereby rendering the oxygen sensor portable with the stored electrolyte and usable within a few minutes of operation.

31 Claims, 3 Drawing Sheets

TO SENSOR CIRCUIT OF FIG. 4

ELECTROCHEMICAL GAS SENSORS AND METHODS FOR SENSING ELECTROCHEMICAL ACTIVE GASES IN GAS MIXTURES

FIELD OF INVENTION

This invention relates to improved galvanic cell type structures for gas sensors for electrically signalling, accurately, the concentrations of electrochemical active gases in gas mixtures and improved methods of sensing gases including in sub-parts per billion range, by continuously removing the active gases from the sensor electrolyte during sensor operation without resorting to an external sparge.

BACKGROUND OF INVENTION

Galvanic type gas sensors for sensing and electrically signalling the concentrations of electrochemical gases, such as oxygen, in gas sensors are well known in the prior art. Other known gas sensors are identified as polarographic type sensors, paramagnetic type sensors and a solid zirconia electrolyte type sensor. Heretofore, it has been established that the galvanic type oxygen sensor is simple in construction, inexpensive and operable at room temperatures and has varied applications without requiring complicated electronic sensing circuits. Such prior art electrochemical gas sensors are described in U.S. Pat. Nos. 3,767,552, 4,077,861 and 5,085,760.

The galvanic type of electrochemical gas sensors comprises a sensing cell having a gas sensing cathode electrode and an anode electrode and an electrolyte for wetting the electrodes and developing a galvanic voltage in the electrochemical sensing cell. An appropriate anode material for a galvanic type sensing cell may be cadium or lead for causing a reaction at the cathode electrode with the gas to be sensed in a gas mixture applied to the sensing cell to thereby provide an electrical output current flow between the external anode and cathode terminals representative of the sensed concentration of the electrochemically active gas in the applied gas mixture. The electrolyte for use in these sensors for sensing oxygen may be an alkaline electrolyte such as potassium hydroxide, KOH. The electrolytic reduction of oxygen, is represented by equation (1), hereinbelow, occurs at the cathode electrode while simultaneously a reaction occurs at the lead anode electrode; that is represented by equation (2) as follows:

$$O_2 + 2H_2O + 4e^- \rightarrow 4OH^{3+} \quad (1)$$

$$2Pb + 4OH^- \rightarrow 2PbO + 2H_2O + 4e^- \quad (2)$$

The reaction product disolves in the basic electrolyte and renews the lead surface of the anode electrode after each reaction. This same principle can be used when the electrolyte utilized in the gas sensing cell is acidic. In the latter case, the reaction at the cathode electrode is represented by equation (3) hereinbelow, while the reaction at the anode electrode is represented by equation (4) as follows:

$$O_2 + 4H^+ + 4e^- \rightarrow 2H_2O \quad (3)$$

$$2Pb + 2H_2O \rightarrow 2PbO + 4H^+ + 4e^- \quad (4)$$

The reaction product in this acidic electrolyte is also an oxide (or in the case if a cadium anode electrode, an oxide of cadium) which dissolves in the electrolyte. This establishes that it is not necessary to have only basic electrolyte for the normal operation of galvanic oxygen sensors.

The polarographic type of gas sensing cell differs from a galvanic type by the need for an external polarizing voltage applied between the cathode and anode electrodes to produce the desired output current.

The known galvanic type of gas sensors are capable of measuring oxygen from a parts per million to parts per billion in gas mixtures with appropriate electronic sensing circuits. Various manufactures of present day oxygen sensors utilizing conventional galvanic gas sensors can sense gases in the parts per million, ppm, range or higher and conventional electronic sensing circuits. The measurement of electrochemical active gases, such as oxygen, in the range of 0.1 to 10 parts per billion in a gas mixture is very difficult to achieve and no acceptable gas sensing cell is presently available for sensing in these sub-parts per billion range. The problem of sensing the active gases in the sub-parts per billion range is that the liquid electrolyte necessary for the proper operation of a galvanic type of sensing cell contains dissolved active gases, such as oxygen. It is known that the concentration of the dissolved oxygen in the electrolyte is extremely high compared to the sub-parts per billion level of the gas to be sensed in the gas mixture applied to the gas sensor. Stated differently, the background level of the dissolved oxygen is much higher than the small electrical output signal derived from the sensor due to the very small quantities of oxygen. It has been found that in order to detect or sense the very small concentrations, sub-parts per billion, of oxygen, it is necessary to eliminate or remove the relatively high concentration of dissolved oxygen concentration in the liquid electrolyte.

A gas sensor for sensing electrochemically active gases in the parts per billion range in a gas mixture is disclosed in U.S. Pat. No. 5,085,760. The gas sensor disclosed in the U.S. Pat. No. '760 patent teaches the use of a high surface area, gas diffusing cathode electrode in a galvanic type of gas sensor for producing low levels of oxygen detection in a gas mixture. The amount of electrolyte needed to obtain very low levels, ppb, of sensing by using the gas sensing electrode taught in the U.S. Pat. No. '760 patent is small compared to conventional cathode electrodes for sensing in the parts per million, ppm, range to obtain the same results. It has been found that even this small amount of electrolyte has enough dissolved oxygen therein that it is difficult to obtain accurate output signals when it is necessary to detect less than one part per billion of an active gas such as oxygen. To utilize such gas sensing structures for sensing in sub-parts per billion, 0.1 to 10 parts per billion of oxygen, it is necessary to continuously apply an ultra pure inert gas to the electrolyte for sparging the dissolved active gases from the electrolyte. This procedure usually takes a couple of days and sometimes weeks to remove the dissolved gases from the electrolyte. This sparging procedure requires the use of ultra clean tubing and a scrubber to produce an ultra clean, inert, sparging gas and the necessary valves for controlling the flow of the sparging gas to permit sensing of oxygen in the sub-parts per billion range. This sparging procedure is required to be continuously in operation during the operation of the gas analyzer. The requirement of continuous sparging renders it difficult to use when a portable gas sensor is required. The sparging procedure introduces turbulence in the liquid electrolyte that produces a noise signal on the electronic monitoring device for the sensor. This noise signal is prominent when the very low levels of active gases are to be sensed. If the sparge rate of the sparging gas is reduced, it permits the dissolution of the active gases in the electrolyte but causes the output base line to go up with time and introduces an error in the results.

A known method of removing the dissolution of the dissolved oxygen in the electrolyte for an oxygen sensor is disclosed in U.S. Pat. No. 4,960,497, for a polarographic type of gas sensor. This known method contemplates the use of a second polarographic sensor having an individual cathode and anode electrode arranged with the sensor electrode. As disclosed the second anode is arranged in an additional electrolyte reservoir but in communication with the principal electrolyte. In addition to the required external potential for the two sensing electrodes, an additional electrical potential is applied to the thus spaced and arranged electrodes for consuming the dissolved gases in the electrolyte. This prior art technique is expensive, makes the overall sensing system bulky and requires additional electronic circuitry.

The above described prior art sensors require a large electrolyte volume to carry out the gas detection in the sub-parts per billion range, even when a gas diffusing sensing electrode having a high surface area catalyst thereon is utilized, as disclosed in said U.S. Pat. No. '760 patent. These sensors are shipped to the ultimate user without any electrolyte and therefore the user must add the electrolyte immediately prior to its use. The minimum quantity of electrolyte required for proper operation is approximately 100–200 milliliters. Prior to actual usage, it is necessary to remove most of the dissolved oxygen by sparging. Accordingly, there is a present need in the gas sensing art for an improved, accurate, electrochemical, galvanic type of gas sensor for detecting or sensing active gases such as oxygen in the 0–10 parts per billion, ppb, range without resorting to sparging of the electrolyte, be relatively inexpensive, portable, and ready to use, without requiring the addition of an electrolyte, after it is received by the end user.

SUMMARY OF INVENTION

The present invention provides an improved and accurate, electrochemical gas analyzing sensor that is capable of sensing sub-parts per billion, 0–10 ppb, of electrochemically active gases, such as oxygen, in a gas mixture without experiencing the aforementioned problems of the prior art devices. The improved gas sensor may utilize a liquid electrolyte or a sol-gel type of electrolyte that permits the gas sensor to be portable and shipped to the end user with the sol-gel type electrolyte therein whereby the end user may utilize the gas sensor in a few minutes after receipt. The sol-gel is advantageously formed in the gas sensor container and forms a microporous silicon dioxide, $SiO_2$, polymer. In the present invention, the sol-gel is advantageouly used to increase the output signal to noise ratio and to protect the loss of the liquid electrolyte.

The improved gas sensor removes or minimizes the dissolved active gases from the electrolyte by means of scavenger electrode means arranged within the electrolyte and coacting with the sensor anode electrode as another galvanic type gas sensor for removing the dissolved active gases from the electrolyte leading to the accurate sensing of gases in the sub-parts per billion. The scavenger electrode means comprises a scavenging cathode electrode means arranged in intimiate, insulatively relationship with the gas sensing cathode electrode for receiving the diffused active gases and reacting the gases such as oxygen before being dissolved in the bulk electrolyte. A plurality of scavenger electrodes is preferred for sensing gases in the sub-parts per billion. The same concept of a scavenging electrode may be utilized in conventional gas sensors for sensing gases in the parts per million.

From a broad structural standpoint, the present invention contemplates the use of a galvanic type of gas sensor for sensing active gases in the parts per billion range along with scavenger electrode means built into the sensor for reacting the active gases as another galvanic gas sensor coacting with the sensor anode for reacting the active gases before being dissolved in the bulk electrolyte rendering the gas senor capable of sensing active gases in the sub-parts per billion range. The scavenger electrode means is positioned in relationship to the sensing gas electrode for optimizing the response characteristics of the gas sensor, preferably arranged in an insulative relationship with the gas sensing electrode for reacting the active gases prior to being dissolved in the bulk electrolyte or sol-gel electrolyte. A plurality of additional scavenger electrodes are preferably spaced in the electrolyte and all electrically connected in common to further remove dissolved gases from the electrolyte. When the liquid electrolyte is stored in a sol-gel, it takes on the characteristics of a "solid-state" electrolyte that permits the gas sensor to be shipped with the sol-gel type of electrolyte thereby rendering the sensor portable but also ready for parts per billion gas analysis within a few minutes of its receipt by the end user. The sol-gel may be formed in the sensor container and increases the output signal to noise level and to protect the electrolyte. The improvements disclosed herein are also useable in conventional galvanic sensors to analyze gas mixtures in the parts per million range.

From a broad method of sensing concentrations of an electrochemical gas in a gas mixture by means of a galvanic sensing cell capable of sensing gases in parts per million through sub-parts per billion range the method includes including the step of adding scavenger electrode means to a preselected gas sensing cell for reacting any active gases dissolved in the electrolyte or partially reacted by galvanic action within the sensing cell to permit the sensing cell to accurately provide output signals representative of the concentrations of an active gas in a gas mixture. The method further includes the step of storing a liquid electrolyte in a "solid-state" medium such as a sol-gel to render the sensing cell portable with the electrolyte and further improve the output signal to noise ratio of the output signals from the gas sensor.

BRIEF DESCRIPTION OF THE DRAWINGS

These and other features of the present invention may be more fully appreciated when considered in light of the following specification and drawings, in which.

DETAILED DESCRIPTION OF THE PREFERRED EMBODIMENTS OF THE INVENTION

Figure 1:
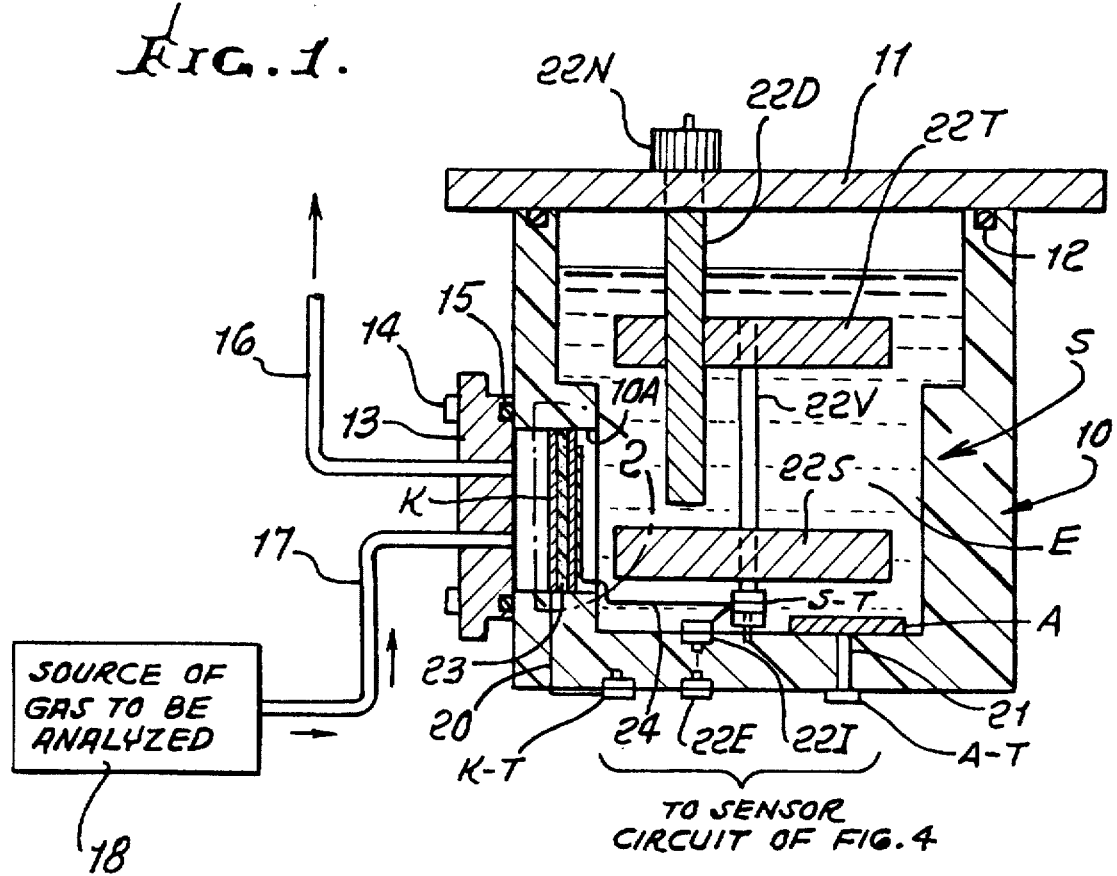
FIG. 1 is a cross-sectional, front view of an electrochemical gas sensor embodying the present invention.

Now referring to the drawings, the detailed description of the improved electrochemical, galvanic gas sensing cell S of the present invention will be described. The sensor S is incorporated in a housing or a container constructed of an electrically insulative plastic material, such as acrylic or polycarbonate, 10 having a U-shaped configuration with an open end. The housing 10 is closed by means of a stainless steel cover 11 and rendered leak proof by the provision of an O-ring 12. The general configuration of the housing 10 is similar to the housing for the sensing gas concentrations in the parts per billion range disclosed in U.S. Pat. No. 5,085,760 assigned to the same assignee as the present invention. As in the patented structure, one side wall of the housing 10 is provided with a circular aperture 10A to accomodate the sensing cathode electrode K along with a scavenging electrode in accordance with the present invention. The aperture 10A is sealed off by the provision of a cover element 13 secured to the housing 10 by means of a plurality of fasteners 14 and an O-ring 15. The cover member 13 is provided with a pair of spaced apertures for accomodating a pair of gas tubes 16 and 17 for conveying and distributing the gas mixture to be analyzed or sensed to the cathode electrode K. The gas tube 17 is coupled to receive the gas mixture from the source of gas to be analyzed illustrated as the block 18. The gas tube 17 conveys the gas mixture into the aperture 10A for impinging against the cathode K and along the outer exposed surface of the cathode K and exits the housing 10 by means of the gas exit tube 16.

The gas sensing cathode K for use in the present invention may be any cathode electrode capable of sensing gas concentrations in the parts per billion range including the high surface area metal catalyst diffusion electrode as disclosed in U.S. Pat. No. 5,085,760, incorporated herein by reference. For the purposes of the present invention, the cathode electrode K can be a gas diffusion metallic electrode coated on a microporous structure of polytetrafluoroethylene ("Teflon") and carbon mixture or a porous metallic disk. Specifically, the gas sensing cathode electrode K is a silver/carbon gas diffusion electrode K and is internally connected by means of a lead wire 20 to the cathode external terminal K-T mounted to the housing 10, as illustrated. The position of the principal scavenger electrode 22 relative to the gas sensing electrode K is very important in the scavenging of the liquid electrolyte E for dissolving any active gases in the bulk electrolyte stored in the housing 10, as will be described more fully hereinafter. The electrolyte E can be any well known basic electrolyte utilized in electrochemical galvanic gas sensors such as an aqueous electrolyte solution such as a potassium hydroxide aqueous solution. The remaining portion of the gas sensor is the anode electrode A which may be constructed of lead, cadium or the like and is illustrated as a circular disc mounted on the inside bottom wall of the housing 10 and is electrically connected to the external terminal A-T by a conductive stud 21.

Figure 2:
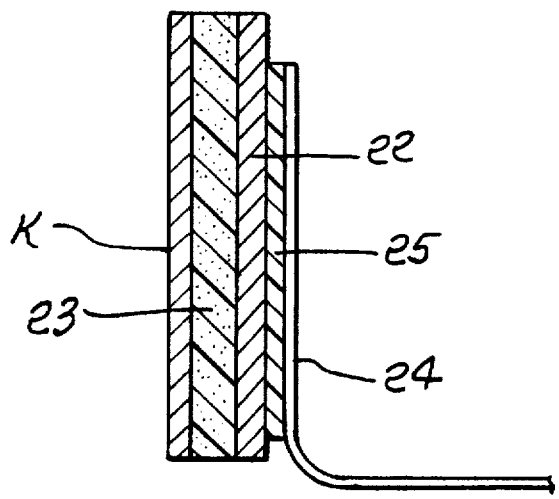
FIG. 2 is an enlarged view of gas sensing electrode and scavenging electrode physical arrangement taken at the partial circle 2 of FIG. 1.

The positioning of the scavenging electrode 22 relative to the gas sensing cathode electrode K is best illustrated in FIG. 2. The gas sensing electrolyte K is illustrated as comprising a silver/carbon gas diffusion electrode K that is electrically separated from the scavenger electrode 22 in the form of a silver screen by a porous polyethylene barrier 23. The barrier 23 permits diffusion of the electrolyte and also protects the sensing cathode K from getting scratched. The size of the scavenging electrode 22 is at least the same size as the sensing electrode K or greater in area so that any diffused active gas such as oxygen reacts at the scavenging electrode 22 surface before being dissolved into the bulk electrolyte E. A silver wire 24 is electrically connected to the scavenger electrode 22 by the provision of a silver paste/epoxy 25 making electrical contact between the two. The scavenging electrode 22 functions as an electrochemical sensor within the sensor S with the common anode electrode A for reacting the active gases in the electrolyte E. The opposite end of the silver wire 24 is electrically connected to an internal scavenger terminal 22I and in turn to an external scavenger terminal 22E. The illustrated insulative, side by side, relationship of the gas sensing electrode K and the scavenging electrode 22 is important to the reaction of the active gases to prevent any unreacted or partially reacted gases from entering the bulk electrode E without being reacted at either the gas sensing electrode K or the scavenger electrode 22. Any variation in this relationship has been found to detrimentally change the response characteristics of the sensor S.

It should be noted that the electrochemical gas sensor S of the present invention does not require the tubing and controls for applying a purging gas through the bulk electrolyte E for removing any residual gases from the electrolyte either prior to or during the gas sensing operations. The scavenging electrode 22 was utilized for this purpose. The complete gas sensor S was constructed in accordance with the teachings of the prior U.S. Pat. No. 5,085,760 as disclosed in that patent for sensing active gases, such as oxygen, in the parts per billion range of oxygen in a gas mixture for determining the effectiveness of the electrochemical gas sensor S utilizing scavenger electrode means, without the continuous sparging during the gas sensing operation. For this purpose, the testing of the invention was carried out by the use of additional scavenging electrode 22S in sensor S, as illustrated in FIG. 1, for removing all of the dissolved active gas from the bulk electrolyte. A second scavenging electrode in the form of a silver mesh 22S was placed near the bottom of the housing 10, as illustrated. In operation, the internal galvanic cell of scavenger electrodes 22 & 22S along with the common anode A commences operation as soon as the cathode electrode K and anode electrode A are shorted together, whether or not the sensor S is incorporated in a gas analyzer or not. The product of this reaction dissolves in the electrolyte E and a fresh surface on the anode A is always available to complete the reaction.

In the testing of the prior art sensor pursuant to U.S. Pat. No. 5,085,760, a gas diffusion electrode was utilized as a gas sensing cathode electrode having an area about 1.130 square inches. The anode electrode was constructed of lead. The prior art sensor was provided with a metallic sparger to sparge the liquid electrolyte with a pure inert gas. The sensor was filled with a presparged electrolyte, having been sparged with a pure inert gas, or an electrolyte of 10% potassium hydroxide (10% KOH). The prior art sensor was installed in a sample system with suitable sensing circuitry and operated while continuously sparging the sensing cell electrolyte to remove the dissolved active gas from the commencement of the operation of the cell. The drop in the output of the analyzer was recorded and plotted. The sensor S of the present invention utilizing only the above scavenger electrodes 22 & 22S were operated with all of the above perameters being constant but without any sparging of the electrolyte. Again, the results of the scavenger electrode sensor were recorded and plotted. It was determined that with the use of the scavenger electrodes less than 5 hours elapsed for the sensor S to come down to 100 parts per billion level and remove the dissolved active gases from the electrolyte. The prior art sensor (without a scavenger electrode) took around 35 hours to come down to this same level of dissolved active gases in the electrolyte even when the external sparger was continuously utilized. This significant difference established the value of the use of a scavenger electrode without resorting to any sparging and thereby eliminates the need for such hardware and apparatus. Initially, the scavenging process by means of the electrodes is very fast and after a few hours of operation, the process slows down since there is no more available active gas in the electrolyte and an equilibrium stage is reached. The state of equilibrium can be monitored on a recording device and seen to produce a constant output current. Since the electrochemically active gases in the electrolyte are in low concentrations, either in the parts per million or parts per billion, the depletion of the anode electrode is very slow and the anode electrode should last for years.

Despite the above favorable test results utilizing the pair of scavenger electrodes 22 and 22C, it is deemed preferable to use additional scavenger electrodes such as the three silver screen electrodes 22D, 22T, and 22V, illustrated in FIG. 1 and all connected electrically together by means of an internal terminal S–T also connected to the silver lead wire 24 and in turn to the external terminal 22E for all of the scavenger electrodes. The use of these additional electrodes further assures of the rapid removal of the dissolved active gases from the electrolyte E including those not reacted at the principal electrode 22 and the secondary scavenger electrode 22S. The electrode 22T is positioned in the electrolyte E in a spaced, substantially parallel relationship with electrode 22S. The vertical electrode 22V extends upwardly from the terminal S–T to the electrode 22T and parallel to the electrode 22D. The scavenger electrode 22D is suspended downwardly from the cover plate 11 and secured thereto by means of a nut 22N. This use of the scavenging electrodes in the sensor S, of the present invention, permits a gas mixture to be analyzed containing oxygen, for example, in sub-parts per billion level of electrochemically active gases and without producing noise and without resorting to the sparging of the electrolyte. It should be noted that although the scavenging electrodes were described as a silver mesh, they may be constructed of other metals such as gold, platinum or other metals capable of reducing oxygen inside the bulk electrolyte of the sensor S or a metal coated surface having the aforementioned capabilities.

Figure 4:
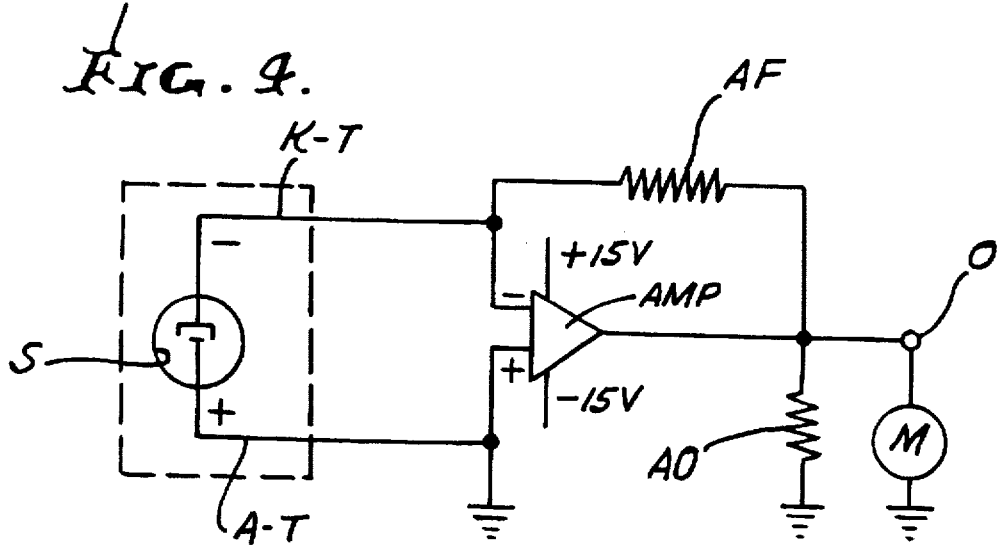
FIG. 4 is an electrical schematic diagram of a sensing circuit for use with the gas sensors of FIGS. 1 and 3.

Now referring to FIG. 4, the electrical circuit for processing the electrical signals derived from the output terminal A–T and K–T, respectively the anode and cathode external terminals will be described. The sensor output current flowing externally between the output terminals is on the order of 12 to 16 micro-amperes per parts per million of oxygen in a gas to be analyzed when the gas sensing cathode electrode K has an area of about 1.130 square inches. Any conventional sensing circuit may be utilized by coupling it between the sensor S's output terminals as illustrated in FIG. 4. A conventional operational amplifier Amp is illustrated with its input terminal connected to the corresponding sensor output terminals A–T and K–T. The output circuit for the amplifier Amp is connected in series circuit relationship with an output resistor AO connected to a common voltage level or ground. A feedback resistor AF is connected between the output terminal common to the resistors AF and AO, to the negative input terminal of the amplifier Amp. A meter M may be connected between the output terminal O and ground that is calibrated to read the concentration of the sensed oxygen or active gas undergoing analysis for a direct read-out of the sensor S.

Figure 3:
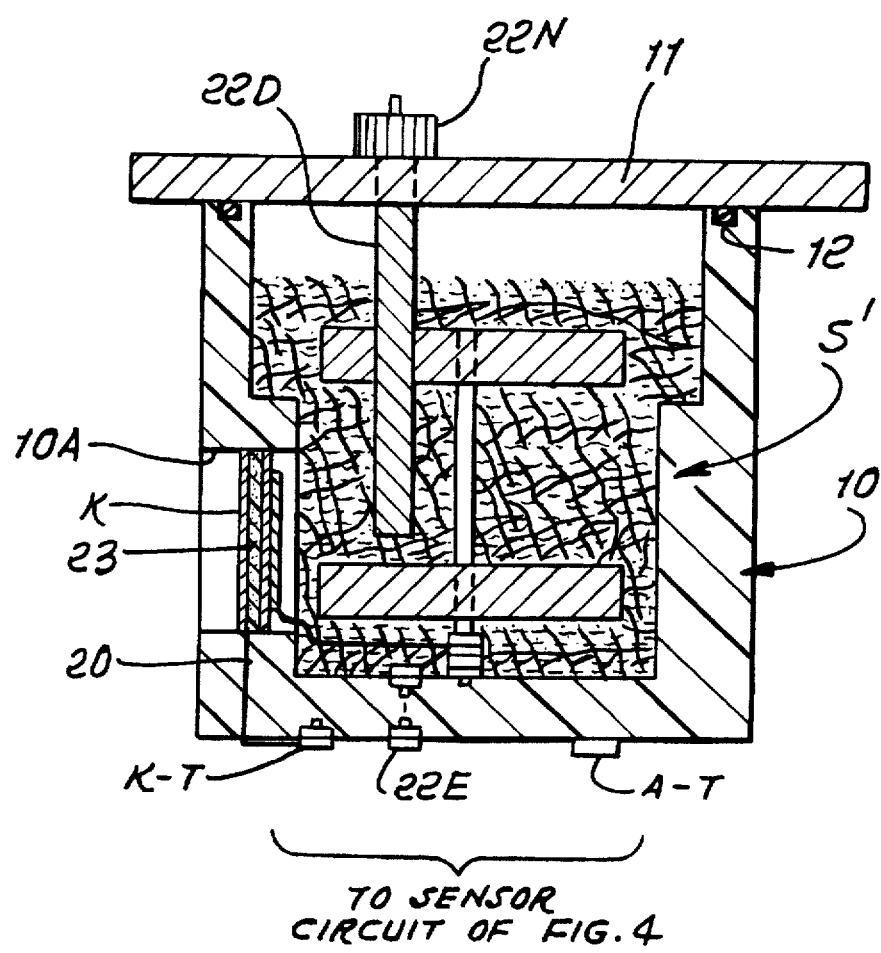
FIG. 3 is a cross-sectional front view of the gas sensor of FIG. 1, with parts omitted, and illustrating the storage of the electrolyte in a sol-gel medium wherein the bold lines represent the sol-gel and the light lines the trapped electrolyte within the sol-gel.

Referring to FIG. 3, a modified gas sensor S' is illustrated. The sensor S' is the same as the sensor S of FIG. 1 except the liquid electrolyte E is stored in a porous or semi-solid medium having a plurality of pockets for entrapping the electrolyte therein. The gas source and tubing for conveying the gas mixture to be analyzed are intentionally omitted from FIG. 3 but are required in any practical embodiment of the invention. The storage medium for the electrolyte employed in the present invention is a Sol-Gel, a microporous silicon dioxide, $SiO_2$, polymer prepared and formulated for the purposes of the present invention so that the electrolyte has the same electrochemical characteristics as the liquid electrolyte E but physically is a "solid state" electrolyte. The sol-gel prepared in accordance with the present invention is a semi-solid having voids therein throughout the sol-gel wherein the liquid electrolyte is immobilized in the voids of the sol-gel. In FIG. 3 the dark, bold lines represent the sol-gel while the light lines represent the liquid electrolyte trapped inside the sol-gel medium and is dispersed through-out the medium. The sol-gel polymer as formulated and produced in accordance with the present invention to have the correct characteristics for use in the sensor S' and are not commercially available. Sol-Gels per se are known in the art and are described in the publication "Gel-Silica Science" by L. L. Hench and W. Vasconcelos in the Annual Review Material Science, 1990, Vol. 20, pages 269–298.

For the purposes of the present invention, the sol-gel is formed by an acid catalyst using hydrochloric acid. The ratio of the various components utilized are: TMOS (Tetramethyl orthosilicate):$H_2O$ (water):Methyl alcohol:hydrochloric acid=1:2:2:0.1. These components are mixed inside the housing 10 and are allowed to form a gel overnight. The sol-gel becomes rigid and takes the shape of the internal cavity of the housing 10. The sensor S' is assembled just like a normal electrochemical oxygen sensor that utilizes a liquid electrolyte, i.e. see FIG. 1. The next step in the preparation is that a layer of electrolyte is placed on the top of the sol-gel as formed in the housing 10 and allowed to equilibrate for a few hours whereby the liquid electrolyte is trapped in the voids of the sol-gel so as to immobilize the electrolyte therein as illustrated in FIG. 3. By utilizing the sol-gel type of electrolyte for the sensor S', the sensor can be shipped with the sol-gel and electrolyte therein and therefore the sensor is ready for parts per billion analysis within a few minutes of the commissioning thereof. In accordance with the present teachings, the sol-gel electrolyte is used to increase the output signal to noise ratio from the sensor and to protect the loss of electrolyte. In use, the sensor S' having scavenger electrodes and the sol-gel electrolyte was allowed to drop down to parts per billion, ppb, level using the scavenging of the oxygen from the electrolyte. The sensor S' was then exposed to the environmental air for 30 minutes and then was tested in a gas analyzing system. The sensor S' did not take any time to detect a ppb, parts per billion, level of oxygen. When the sensor S with the scavenger electrodes and the liquid electrolyte per FIG. 1 was exposed to 10 parts per million, ppm, of oxygen for a few minutes and the sensor operation was initiated, in less than 10 minutes the output of the sensor S came back to the same parts per billion, ppb, level where it was exposed to a high oxygen concentration.

Figure 5:
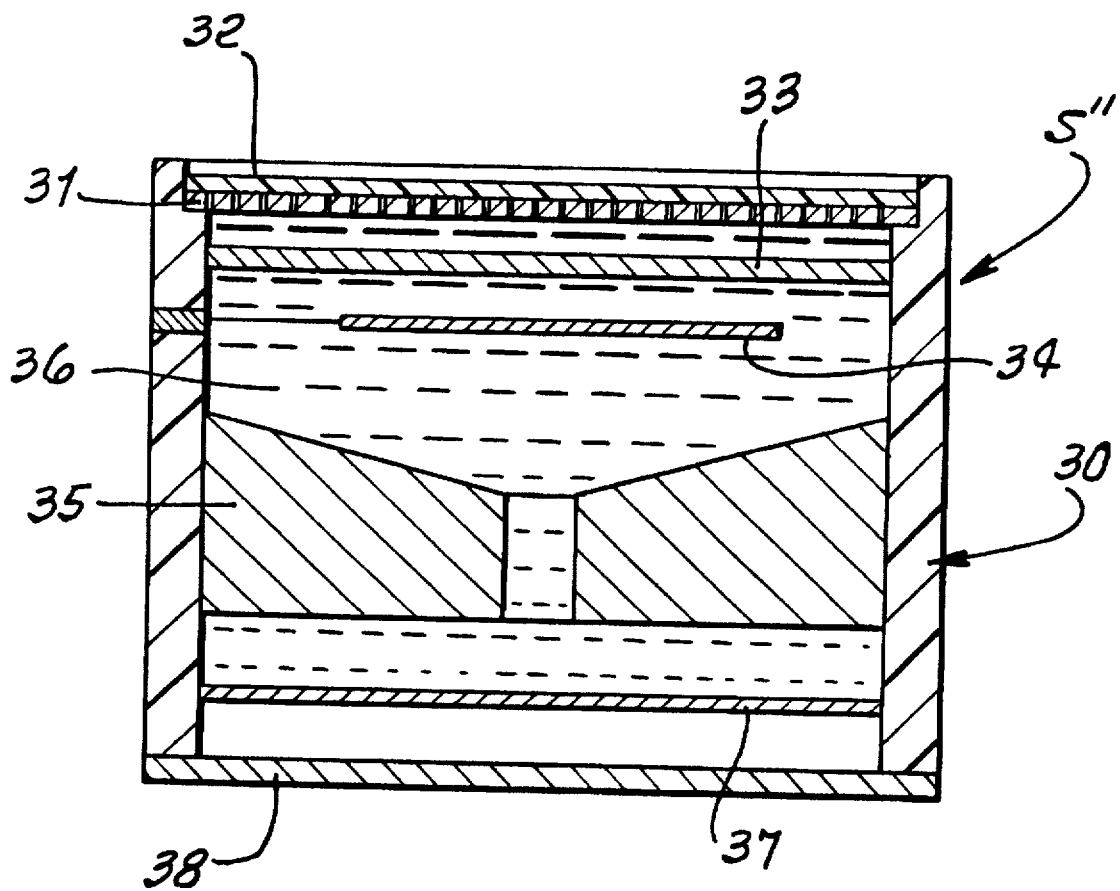
FIG. 5 is a cross-sectional view of a conventional gas sensor utilizing a scavenger electrode.
Figure 6:
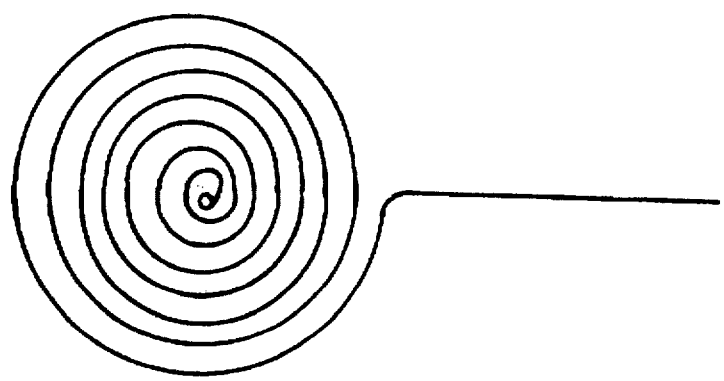
FIG. 6 is a preferred configuration of a scavenger electrode for the gas sensor of FIG. 5.

FIG. 5 illustrates a conventional electrochemical, galvanic sensing cell including a scavenging electrode as disclosed hereinabove. This conventional sensing cell is used for sensing gas mixtures having an active gas in the parts per million level. U.S. Pat. No. 3,767,552 discloses a gas sensor that is exemplary of this type of conventional sensor. The sensor S" has a housing 30 constructed of an electrically insulative material such as polyethylene with an open top. The cathode electrode 31 is a perforated metal cathode, as illustrated, and closes the open top end of the housing 30. A teflon membrane 32 is secured to the top of the housing 30 over the cathode 31 that diffuses the gases therethrough to impinge on the top surface of the cathode electrode 31 and prevents the sensor electrolyte to leak out. The anode electrode 35 is constructed of lead with a central aperture and mounted within the housing 30 adjacent the lower end thereof. The housing 30 is filled with a liquid electrolyte 36 such as 10% potassium hydroxide, KOH, as illustrated. The back plate 38 encloses the bottom end of the housing 30. A flexible membrane 37 is mounted to the housing 30 above the back plate 38 and spaced therefrom. The membrane 37 accomodates the pressure variations of the electrolyte 36. The electrolyte extends below the anode electrode 35 and is supported on the membrane and wets the anode electrode and the cathode electrode 31. In this embodiment a scavenger electrode is mounted to the housing 30 between the anode and cathode electrodes. The gas sensing cathode electrode 31 is electrically insulated from the scavenger electrode 34 by an insulative paper element 33 mounted to the housing 30 intermediate the two electrodes. The paper 33 is commercially identified as a Whatman filter paper No. 54 available from Whatman International Ltd. of Maidstone, England. The paper 33 can sustain severe acidic or basic conditions it is subjected to in a gas sensor of this type of sensor S". The scavenger electrode 34 is utilized in combination with the anode electrode 35 for reacting any active gases dissolved in the electrolyte for improving the output responses from the sensor S" by rendering them more accurate of the active gases sensed. The preferred configuration of the scavenging electrode 34 is illustrated in FIG. 6 and consists of spiral silver wire that is nine inches long and 0.69 inch diameter. The number of coils for the electrode 34 can be varied depending on the physical size of the sensor S". Although the bulk electrolyte 36 is described and illustrated, the electrolyte may be stored in a sol-gel medium, as described hereinabove, for optimum results.

In operating the sensor S" of FIG. 5, the sensor was allowed to come down from air to the parts per million, ppm, level of oxygen with and without the scavenger electrode 34 and it was determined that the time required to come down to less than 10 ppm oxygen level is twice the time without the scavenger electrode as with this electrode.

We claim:

1. An electrochemical, galvanic sensing cell for sensing concentrations of an electrochemical active gas in a gas mixture including in parts per billion and providing an output electrical current flow from the sensing cell accurately representative of the concentrations of the sensed electrochemically active gas including in the sub-parts per billion range, wherein the electrochemical, galvanic sensing cell has a gas sensing cathode electrode means that has a composite structure with an electrically conductive support having a gas diffusion, hydrophobic surface, and an anode electrode means immersed in an alkaline or basic electrolyte all in a single container for causing reactions at the anode and cathode electrodes with an electrochemical active gas undergoing analysis providing an output electrical current flow between the cathode and anode electrodes representative of the sensed gases including in the parts per billion range the improvement comprising scavenger electrode means comprising scavenger electrode means arranged in intimate, insulative relationship with said gas sensing electrode so that any electrochemical gas not completely reacted at said gas sensing electrode continuously reacts at said scavenger electrode means which acts as a galvanic cell with said anode electrode means within said single container prior to said gas being dissolved into a said electrolyte so that said gas sensor is effective for sensing active gases in the sub-parts per billion range without resorting to sparging of the electrolyte.

2. An electrochemical, galvanic sensing cell as defined in claim 1 wherein said gas sensing electrode means and said scavenger electrode means are of substantially the same size.

3. An electrochemical, galvanic sensing cell as defined in claim 1 or 2 including porous, insulative means arranged between said gas sensing electrode means and said scavenger electrode means for electrically isolating said two electrodes, said porous insulative means permitting the diffusion of electrolyte therethrough.

4. An electrochemical, galvanic sensing cell as defined in claim 1 or 2 wherein said electrolyte comprises a microporous silicon dioxide, $SiO_2$, polymer storing a liquid electrolyte which operates in the sensing cell.

5. An electrochemical, galvanic sensing cell as defined in claim 1 constructed and defined for sensing the concentration of oxygen in a gas mixture and wherein said cathode electrode means is constructed of a metal for the effective reduction of oxygen, said anode electrode means is constructed of lead or cadmium, said electrolyte comprising 10–15% potassium hydroxide aqueous solution and said scavenging electrode means is constructed of silver.

6. An electrochemical, galvanic sensing cell as defined in claim 1 wherein said scavenger electrode means comprises further scavenger electrode means spaced from said first mentioned scavenger electrode means within the electrolyte and in electrical contact with said first mentioned scavenger electrode.

7. An electrochemical, galvanic sensing cell as defined in claim 1 further comprising a plurality of scavenger electrode means arranged within the electrolyte spaced from said first mentioned scavenger electrode means and from each other and all electrically connected to said first mentioned scavenger electrode means for continuously removing any dissolved active gas in the bulk electrolyte.

8. An electrochemical, galvanic sensing cell for sensing concentrations of an electrochemically active gas in a gas mixture and providing an output electrical current flow from the sensing cell representative of the concentrations of the sensed electrochemically active gas wherein the sensing cell has a gas sensing cathode means and an anode electrode means immersed in an alkaline or basic liquid electrolyte for causing reactions at the anode and cathode electrodes with an electrochemical active gas applied to the gas sensing electrode and providing an output external electrical current flow representative of the sensed gases between gas sensing cathode electrode and the anode electrodes the improvement comprising an electrolyte storage medium in the sensing cell having said liquid electrolyte entrapped therein and said storage medium comprises a microporous silicon dioxide polymer.

9. An electrochemical, galvanic sensing cell for sensing concentrations of an electrochemical active gas in a gas mixture and providing an output electrical current flow from the sensing cell representative of the concentrations of the sensed electrochemically active gas wherein the sensing cell has a gas sensing cathode electrode means and an anode electrode means immersed in an alkaline or basic liquid electrolyte for causing reactions at the anode and cathode electrodes with an electrochemical active gas applied to the gas sensing electrode and providing an output external electrical current flow representative of the sensed gases between gas sensing cathode electrode and the anode electrodes wherein the improvement comprises a liquid electrolyte stored in a semi-solid having voids therein with said electrolyte immobilized in said voids.

10. An electrochemical sensing cell for sensing concentrations of an electrochemically active gas including the concentrations of oxygen in a gas mixture in the sub-parts per billion range, 0–10 ppb, comprising an electrically insulative container having an aperture in one of the side walls, cathode electrode means mounted to the apertured wall of the container where only one surface of the electrode is exposed to the inside of the container, anode electrode means supported within the container, an electrolyte which is stored within the container for wetting said anode electrode means and said one surface of said cathode electrode means, a scavenger cathode electrode means insulatively mounted with said cathode electrode means adjacent said one surface of the electrode exposed to the inside of said container and wet by said electrolyte, porous, insulative means positioned adjacent said one side of said cathode means and positioned with said scavenger electrode means to prevent any short circuiting between said cathode and said scavenger cathode electrode means while permitting the diffusion of the electrolyte therethrough to said cathode electrode means, said scavenger cathode electrode means being constructed and defined for galvanic action with said anode electrode means for continuously removing any electrochemically active gases including oxygen reaching said scavenging electrode means before being dissolved in the electrolyte, said cathode electrode means being constructed and defined as a composite structure with an electrically conductive support having a gas diffusion, hydrophobic surface arranged on the opposite side of said one surface exposed to the inside of the container for conveying gas therethrough for permitting measurements in the parts per billion range and a silver or gold catalyst with a surface area of approximately 150 square meters per gram dispersed on the electrically conductive support and wetted by an electrolyte stored in the container to cause the electrochemically active gas conveyed through the gas diffusion surface to react at the catalyst surfaces, the hydrophobic surface blocking the flow of electrolyte outside of said catalyst surface, means for continuously circulating said gas mixture to be analyzed for exposure to the gas diffusion surface of the cathode electrode means to be diffused therethrough to the catalyst layer so that the active gas is reacted at the catalyst surface, said galvanic scavenger cathode electrode means being further characterized as being operative to cause any electrochemical active gas present thereat and not completely reacted at the cathode electrode surface to react at the scavenger cathode electrode means preventing its dissolution into the electrolyte and an electrical output current flows from said cathode and anode means during the operation of said thus defined sensing cell that is accurately representative of the concentrations of the sensed electrochemically active gas in the sub-parts per billion range.

11. An electrochemical sensing cell as defined in claim 10 wherein said electrolyte is an aqueous solution comprising potassium hydroxide.

12. An electrochemical sensing cell as defined in claim 10 wherein said electrolyte is a solid state electrolyte comprising a microporous silicon dioxide polymer stored in said container including during shipping or transporting of said sensor.

13. An electrochemical sensing cell as defined in claim 10 wherein said cathode electrode means and said scavenger cathode electrode means are of substantially the same size so that any diffused active gas including oxygen reacts at the scavenging electrode means before being dissolved in the electrolyte.

14. An electrochemical, galvanic gas sensing cell for sensing concentrations of an electrochemical active gas in a gas mixture comprising an electrically insulative container having an open end that is for storing an electrolyte in the container, a gas permeable, liquid impermeable membrane, secured to said open end of said container having a preselected thickness for limiting the diffusion of gases to be sensed and to be conveyed therethrough, a porous, metallic cathode electrode means arranged within said container in intimate contact with said membrane for receiving and reacting the electrochemically active gases conveyed through said membrane, anode electrode means arranged within said container in a spaced relationship with said cathode electrode means, a liquid electrolyte stored in said container and wetting the cathode and anode electrode means for causing the reaction of the electrochemically active gases conveyed through said membrane, scavenger cathode electrode means which is mounted to and supported by the electrically insulative container and supported between said anode and cathode electrode means, and electrically insulative means mounted within said container between said cathode electrode means and said scavenger cathode means for preventing said electrodes from short circuiting and each being operative with said anode electrical means for reacting the electrochemical active gases diffused to said cathode electrode means with any of said gases dissolved into said electrolyte being reacted by means of said scavenger electrode means before being dissolved into the bulk electrolyte between said scavenger and anode electrode means.

15. An electrochemical gas sensing cell as defined in claim 14 wherein said scavenger electrode is constructed and defined to be an electrically conductive wire having a spiral configuration of a plurality of spaced coils.

16. An electrochemical gas sensing cell as defined in claim 15 wherein said electrically conductive wire is silver.

17. An electrochemical gas sensing cell as defined in claim 14 or 15 wherein said electrically insulative means comprises an electrically insulative paper which sustains severe acidic or basic conditions of said electrolyte.

18. An electrochemical gas sensing cell as defined in claim 17 wherein said electrolyte is stored in a microporous sol-gel storing the electrolyte therein.

19. An electrochemical gas sensing cell as defined in claim 18 wherein said sol-gel is a silicon dioxide polymer formed in said sensing cell.

20. A method of sensing concentrations of an electrochemically active gas in a gas mixture by means of a galvanic sensing cell which senses electrochemically active gases in the sub-parts per billion range including the steps of providing a gas sensing cell which produces electrical output signals representative of the concentrations of an active gas in a gas mixture applied to said gas sensing cell by galvanic action of the cell sensing electrodes wet by an electrolyte, and continuously removing any reactive gases in said electrolyte of the cell wherein the cell senses and accurately provides output signals representative of the concentrations of an active gas in a gas mixture including down to sub-parts per billion, 1–10 ppb without resorting to purging the reactive gases from the electrolyte by using a plurality of scavenger electrode means.

21. A method for sensing concentrations of an electrochemical active gas in a gas mixture by means of a galvanic gas sensor capable of sensing active gases up to parts per billions in a gas mixture including sub-parts per billion, providing a galvanic gas sensor having a gas sensing cathode electrode having a preselected area, an anode electrode and an electrolyte for wetting said electrodes, all selected for sensing a preselected active gas or gases and all contained in a single sensor container, and continuously removing any unreacted or partially reacted gases in the electrolyte so that the gas sensor senses and signals accurate concentrations of active gases including in a range of 0–10 parts per billion and more in a gas mixture by using scavenger electrode means being at least the same size in area as the sensing electrode.

22. A method for sensing as defined in claim 21 wherein said electrolyte is stored in the sensor in the form of a microporous silicon dioxide polymer thus rendering the gas sensor portable and shippable with the electrolyte therein.

23. A method for sensing as defined in claim 21 wherein said step of positioning said scavenger electrode means comprises positioning a first scavenger electrode in an insulative spaced relationship to said gas sensing electrode immediately adjacent thereto for receiving the unreacted or partially reacted gases therefrom, and positioning a plurality of additional scavenger electrodes in the electrolyte spaced from said first scavenger electrode and spaced from one another for further removing the active gases from the electrolyte, each of said scavenger electrodes being electrically connected together, each of said scavenger electrodes galvanically functioning with said sensor anode electrode for continuously reacting said gases.

24. A method for sensing the concentrations of an electrochemically active gas in a gas mixture by means of an electrochemical, galvanic sensing cell providing an electrical output current representative of the concentrations of the sensed electrochemically active gases including in sub-parts per billion range, said method including the steps of providing an electrochemical, galvanic sensing cell which senses concentrations of such an active gas in the parts per billion range, said sensing cell having a gas sensing cathode electrode, anode electrode and an electrolyte wherein the electrolyte has a dissolved active gas such as oxygen in the electrolyte in relatively high quantities relative to the quantities of the gas undergoing sensing, and continuously removing any dissolved active gas or partially reacted electrochemical gas from the electrolyte before being dissolved in the bulk electrolyte where said sensing cell continuously detects sub-parts per billion of the sensed active gas in a gas mixture without external sparging of the electrolyte.

25. A method as defined in claim 24 further comprising positioning a scavenging cathode electrode in the electrolyte in spaced relationship with another scavenger electrode and electrically connected to said first mentioned scavenger electrode.

26. A method of measuring the concentration of oxygen in parts per billion range in an electrochemical cell without loss of accuracy due to dissolved oxygen concentrations in the electrolyte, providing an electrochemical sensing cell which senses oxygen in the parts per billion range by a oxygen sensing electrode and an anode electrode immersed in a preselected electrolyte, positioning first scavenger electrode means in the electrolyte in a spaced relationship with the oxygen sensing electrode wherein said first scavenger electrode is at least the same size as said oxygen sensing electrode, positioning an insulative, porous barrier in close relationship with said sensing electrode and said scavenger electrode, said barrier permits the diffusion of electrolyte therethrough and protects the integrity of the oxygen sensing electrode, the scavenger electrode means being effective to react any electrochemical gas not completely reacted at said oxygen sensing electrode, removing any dissolved electrochemically active gases such as oxygen from the bulk electrolyte to permit accurate measurements in the sub-parts per billion level by positioning second scavenger electrode means in the electrolyte in a spaced relationship with the first scavenger electrode.

27. A method of measuring as defined in claim 26 including the step of positioning a third scavenger electrode in the electrolyte in a spaced relationship with said first and second scavenger electrodes and electrically connected in common with said first and second scavenger electrodes.

28. A method of sensing concentrations of an electrochemically active gas in a gas mixture by means of a galvanic sensing cell, providing a galvanic sensing cell having a gas sensing electrode and an anode electrode immersed in a basic electrolyte stored in a container for functioning as a galvanic sensing cell for sensing a preselected electrochemical active gas in a gas mixture and providing an electrical output current representative of the concentration of the sensed electrochemical active gas in the gas mixture, removing or minimizing the concentration of dissolved electrochemical gases in the electrolyte by sensing the electrochemical active gas that is not completely reacted at the gas sensing electrode for preventing its dissolution into the electrolyte and producing a more accurate representation of the sensed gas, by arranging a scavenging electrode spaced within the electrolyte.

29. A method of sensing as defined in claim 28 wherein said scavenging electrode comprises an electrical conductor formed into a spiral having a plurality of spaced coils.

30. An electrochemical, galvanic sensing cell for sensing concentrations of an electrochemical active gas in a gas mixture applied to said sensing cell and providing an output electrical current flow from the sensing cell accurately reresentative of the concentrations of the sensed electrochemically active gas, comprising an insulative container, a gas sensing cathode electrode that has a composite structure with an electrically conductive support having a gas diffusion hydrophobic surface, wherein the gas sensing cathode electrode is mounted to the container for sensing active gases applied thereto, an anode electrode mounted to the container and an electrolyte in said container for wetting the cathode and anode electrodes and providing an external current flow signalling the concentration of an active gas applied to the cathode electrode as a result of electrogalvanic action occuring at the electrodes, scavenger electrode means mounted to the insulative container and functioning with the anode electrode for reacting any active gases dissolved in the electrolyte for more accurately electrically signalling the concentration of the sensed active gases applied to the cathode electrode, and electrical insulative means secured to said container between said sensing cathode electrode and said scavenger electrode means.

31. An electochemical, galvanic sensing cell as defined in claim 30 wherein said electrolyte is stored in a sol-gel medium with voids throughout for storing and immobilizing the electrolyte in the container.

* * * * *

UNITED STATES PATENT AND TRADEMARK OFFICE
CERTIFICATE OF CORRECTION

PATENT NO. : 5,690,808

DATED : November 25, 1997

INVENTOR(S) : Akmal et al

It is certified that error appears in the above-identified patent and that said Letters Patent is hereby corrected as shown below:

In Col 1, line 49, in the last element of equation (1) delete "$4OH^{31}$" and substitute ---$4OH^-$---.

Signed and Sealed this

Twenty-fourth Day of March, 1998

Attest:

BRUCE LEHMAN

Attesting Officer

Commissioner of Patents and Trademarks